United States Patent
Rubtsov

(10) Patent No.: US 9,167,959 B1
(45) Date of Patent: Oct. 27, 2015

(54) ILLUMINATION FOR ENHANCED CONTRAST IN DEBRIDEMENT APPARATUS AND METHOD

(75) Inventor: Vladimir Rubtsov, Los Angeles, CA (US)

(73) Assignee: Optech Ventures, LLC, Torrance, CA (US)

( * ) Notice: Subject to any disclaimer, the term of this patent is extended or adjusted under 35 U.S.C. 154(b) by 278 days.

(21) Appl. No.: 13/072,697

(22) Filed: Mar. 26, 2011

Related U.S. Application Data

(60) Provisional application No. 61/318,147, filed on Mar. 26, 2010.

(51) Int. Cl.
*A61B 1/00* (2006.01)
*A61B 1/018* (2006.01)

(52) U.S. Cl.
CPC ...................... *A61B 1/018* (2013.01)

(58) Field of Classification Search
CPC ................ A61B 1/018; A61B 17/29
USPC ......... 600/104, 154, 199, 554, 211, 249, 245, 600/102, 473; 606/210, 131, 211, 205, 16, 606/190, 167, 15; 294/99.2; 385/133; 362/572
See application file for complete search history.

(56) References Cited

U.S. PATENT DOCUMENTS

| | | | | |
|---|---|---|---|---|
| 2,376,448 A * | 5/1945 | Neugass | .................. | 606/211 |
| 2,642,871 A * | 6/1953 | Thuerig | .................. | 606/207 |
| 3,287,547 A * | 11/1966 | Spedding | .................. | 362/119 |
| 5,667,473 A * | 9/1997 | Finn et al. | .................. | 600/104 |
| 5,746,770 A * | 5/1998 | Zeitels et al. | .................. | 606/207 |
| 5,769,791 A * | 6/1998 | Benaron et al. | .................. | 600/473 |
| 5,772,597 A * | 6/1998 | Goldberger et al. | .................. | 600/473 |
| 5,785,658 A * | 7/1998 | Benaron et al. | .................. | 600/473 |
| 5,807,261 A * | 9/1998 | Benaron et al. | .................. | 600/473 |
| 6,017,358 A * | 1/2000 | Yoon et al. | .................. | 606/205 |
| 6,179,847 B1 * | 1/2001 | Possum | .................. | 606/131 |
| 6,185,356 B1 * | 2/2001 | Parker et al. | .................. | 385/133 |
| 6,502,587 B1 * | 1/2003 | Kellum et al. | .................. | 132/301 |
| 6,504,985 B2 * | 1/2003 | Parker et al. | .................. | 385/133 |
| 6,587,711 B1 * | 7/2003 | Alfano et al. | .................. | 600/476 |
| 6,591,049 B2 * | 7/2003 | Williams et al. | .................. | 385/123 |
| 6,648,902 B2 * | 11/2003 | Colgan et al. | .................. | 606/205 |
| 6,730,019 B2 * | 5/2004 | Irion | .................. | 600/178 |
| 6,739,744 B2 * | 5/2004 | Williams et al. | .................. | 362/552 |
| D497,215 S * | 10/2004 | Shaljian | .................. | D26/51 |
| 6,832,849 B2 * | 12/2004 | Yoneda et al. | .................. | 362/551 |
| D506,574 S * | 6/2005 | Yip | .................. | D28/55 |
| 7,029,277 B2 * | 4/2006 | Gofman et al. | .................. | 433/29 |
| 7,083,613 B2 * | 8/2006 | Treat | .................. | 606/29 |
| 7,178,847 B1 * | 2/2007 | Mui | .................. | 294/99.2 |

(Continued)

*Primary Examiner* — Anhtuan T Nguyen
*Assistant Examiner* — Jae Woo
(74) *Attorney, Agent, or Firm* — Lawrence S. Cohen; Brian Billett

(57) ABSTRACT

Light is directed between the arms of a forceps to illuminate an area under debridement of foreign material with a color selected to enhance contrast of foreign material that needs to be removed. The light comes from a multicolor source such as an LED chip having RGBW dies and is transmitted by a light transmitting element such as an elongated waveguide or a light pipe to illuminate the area under examination. The color is selectable so as to obtain a color that has good contrast for the foreign material. The apparatus has a docking station to install the forceps so that it is properly located with respect to the illumination. A camera can be part of the apparatus to transmit imagery to a display.

5 Claims, 8 Drawing Sheets

(56) References Cited

U.S. PATENT DOCUMENTS

| | | | | |
|---|---|---|---|---|
| 7,189,983 B2 * | 3/2007 | Aguirre et al. | 250/504 R |
| 7,202,489 B2 * | 4/2007 | Aguirre et al. | 250/504 R |
| 7,202,490 B2 * | 4/2007 | Aguirre et al. | 250/504 R |
| 7,211,079 B2 * | 5/2007 | Treat | 606/29 |
| 7,250,611 B2 * | 7/2007 | Aguirre et al. | 250/461.1 |
| 7,297,105 B2 * | 11/2007 | Mackin | 600/120 |
| 7,306,559 B2 * | 12/2007 | Williams | 600/245 |
| 7,329,887 B2 * | 2/2008 | Henson et al. | 250/494.1 |
| D584,449 S * | 1/2009 | Shaljian | D28/55 |
| D587,405 S * | 2/2009 | Edwards | D28/55 |
| D614,355 S * | 4/2010 | Epstein | D28/55 |
| D627,105 S * | 11/2010 | Cho | D28/55 |
| 7,901,351 B2 * | 3/2011 | Prescott | 600/162 |
| 7,954,870 B2 * | 6/2011 | Chen | 294/99.2 |
| 7,959,338 B2 * | 6/2011 | Kazakevich | 362/574 |
| 7,981,071 B2 * | 7/2011 | Goldberg | 604/22 |
| 8,020,909 B1 * | 9/2011 | LaVaque | 294/99.2 |
| 8,080,819 B2 * | 12/2011 | Mueller et al. | 257/13 |
| 8,251,891 B2 * | 8/2012 | Moskowitz et al. | 600/104 |
| 8,356,598 B2 * | 1/2013 | Rumsey | 128/207.29 |
| 8,506,565 B2 * | 8/2013 | DeCarlo | 606/42 |
| 8,617,054 B2 * | 12/2013 | Miyamoto et al. | 600/106 |
| 2001/0001260 A1 * | 5/2001 | Parker et al. | 362/572 |
| 2001/0021108 A1 * | 9/2001 | Shimada et al. | 362/103 |
| 2002/0001202 A1 * | 1/2002 | Williams et al. | 362/572 |
| 2002/0009275 A1 * | 1/2002 | Williams et al. | 385/123 |
| 2002/0035312 A1 * | 3/2002 | Colgan et al. | 600/211 |
| 2002/0058931 A1 * | 5/2002 | Parker et al. | 606/16 |
| 2002/0089586 A1 * | 7/2002 | Suzuki et al. | 348/68 |
| 2003/0095781 A1 * | 5/2003 | Williams | 385/146 |
| 2003/0195559 A1 * | 10/2003 | Colgan et al. | 606/205 |
| 2004/0102804 A1 * | 5/2004 | Chin | 606/190 |
| 2004/0181255 A1 * | 9/2004 | Gio | 606/210 |
| 2005/0090709 A1 * | 4/2005 | Okada et al. | 600/104 |
| 2005/0099824 A1 * | 5/2005 | Dowling et al. | 362/572 |
| 2005/0116176 A1 * | 6/2005 | Aguirre et al. | 250/492.1 |
| 2005/0116177 A1 * | 6/2005 | Aguirre et al. | 250/492.1 |
| 2005/0116178 A1 * | 6/2005 | Aguirre et al. | 250/492.1 |
| 2005/0116179 A1 * | 6/2005 | Aguirre et al. | 250/492.1 |
| 2005/0140270 A1 * | 6/2005 | Henson et al. | 313/501 |
| 2005/0171408 A1 * | 8/2005 | Parker | 600/249 |
| 2006/0004258 A1 * | 1/2006 | Sun et al. | 600/160 |
| 2006/0122592 A1 * | 6/2006 | Treat | 606/27 |
| 2006/0217596 A1 * | 9/2006 | Williams | 600/245 |
| 2007/0019309 A1 * | 1/2007 | Neal et al. | 359/844 |
| 2007/0167678 A1 * | 7/2007 | Moskowitz et al. | 600/104 |
| 2007/0287886 A1 * | 12/2007 | Saadat | 600/115 |
| 2008/0009860 A1 * | 1/2008 | Odom | 606/51 |
| 2008/0114349 A1 * | 5/2008 | Treat | 606/30 |
| 2008/0239070 A1 * | 10/2008 | Westwick et al. | 348/68 |
| 2008/0243181 A1 * | 10/2008 | Schneider et al. | 606/211 |
| 2008/0257359 A1 * | 10/2008 | Rumsey | 128/207.29 |
| 2008/0310181 A1 * | 12/2008 | Gurevich et al. | 362/554 |
| 2009/0021033 A1 * | 1/2009 | Khubani | 294/99.2 |
| 2009/0143639 A1 * | 6/2009 | Stark | 600/102 |
| 2009/0267372 A1 * | 10/2009 | Chen | 294/99.2 |
| 2009/0310345 A1 * | 12/2009 | Holder et al. | 362/231 |
| 2010/0004506 A1 * | 1/2010 | Saadat | 600/109 |
| 2010/0295326 A1 * | 11/2010 | Chen | 294/99.2 |
| 2010/0317923 A1 * | 12/2010 | Endo et al. | 600/178 |
| 2011/0046620 A1 * | 2/2011 | Lewandowski et al. | 606/41 |
| 2013/0023910 A1 * | 1/2013 | Solomon et al. | 606/158 |

* cited by examiner

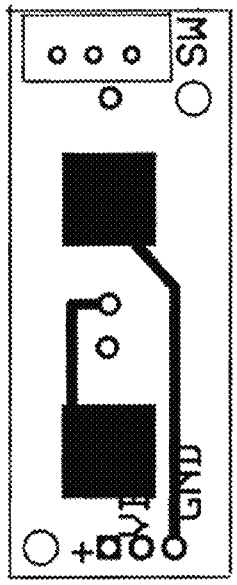
Fig. 6a  LED PCB Front
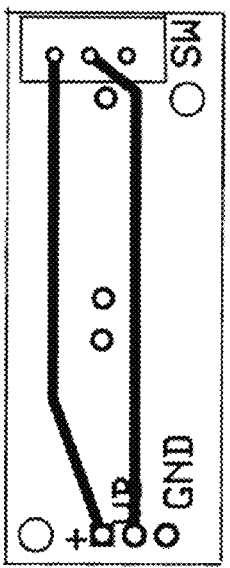
LED PCB Back
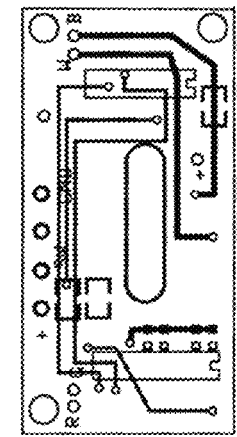
Fig. 6b  DRIVER PCB Front
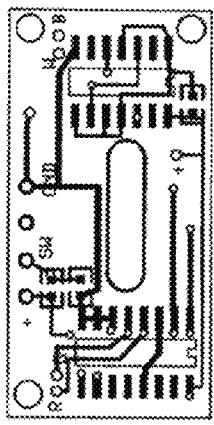
DRIVER PCB Back
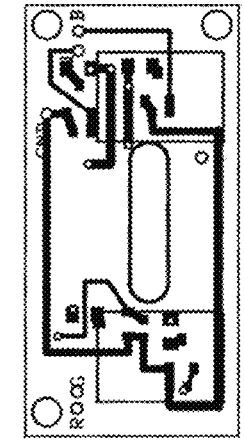
Fig. 6c  POWER SUP PCB Top
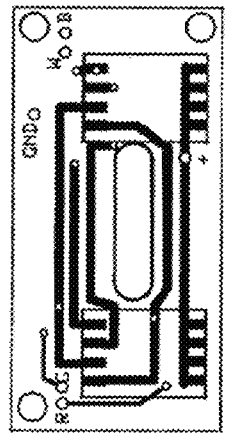
POWER SUP PCB Bottom

ILLUMINATION FOR ENHANCED CONTRAST IN DEBRIDEMENT APPARATUS AND METHOD

CROSS-REFERENCE TO RELATED APPLICATIONS

U.S. provisional application Ser. No. 61/318,147 filed on Mar. 26, 2010 priority of which is claimed and which is incorporated herein by reference.

STATEMENT REGARDING FEDERALLY SPONSORED RESEARCH OR DEVELOPMENT

This invention was made with Government support under contract number 1R43RR031895-01 from the NIH (National Institute of Health)—NCRR (National Center for Research Resources). The Government may have certain rights in this patent.

FIELD OF THE INVENTION

This invention relates to the field of debridement of wounds and surgical openings in particular for foreign material and in particular to illumination in a manner to provide contrasting color for the objects to be removed. It also relates to such illumination accompanied by forceps to implement the removal.

BACKGROUND

Traumatic wounds contain devitalized tissue, bacteria and associated bodies, grass, soil and bone fragments depending on how and where the injury occurred. Wounds caused by blast impact are usually more severe, and are contaminated with an even greater variety of foreign bodies. The debris can include weapon shells, fabric, gravel, ceramic shards and shrapnel. The wound also will contain devitalized skin and muscle tissue The speed and quality of wound debridement in the initial treatment stage are crucial to prevent the type of infections that lead to mortality and morbidity.

A surgeon tending to such wounds, as a rule, presently uses visual observation and mechanical methods (hand, forceps and scalpel) to identify and remove the objects and devitalized tissue. Although ceiling and head mounted lights are often used for illumination, the light scattered from wet tissue and shadows from the surgical instruments dramatically reduce the visual contrast necessary for locating and removing such objects.

SUMMARY

The invention resides in methods and apparatus for enhancing the ability to visualize foreign bodies (also referred to as materials) in a wound or other body opening by illuminating the operational field with one or more selected colors to match hues of specific material, thereby enhancing contrast with the surrounding body parts. The method can be implemented in a multicolor illuminator that can be attached to any type of surgical forceps. In accordance with the principles of this invention, an illuminator is provided for attachment to surgical forceps. The illuminator is provided with a controller and a light-emitting diode (LED) chip, the controller being user operated to select different portions of the light spectrum for the illumination of a wound. In one embodiment, a red, green, blue, and white LED chip is provided. In another embodiment ultra violet light is also provided. The illuminator is configured to provide a dock for the head of a forceps and light pipes are provided to carry light from the LED chip(s) to the distal end of the forceps. a microminiaturize camera can be incorporated in the illuminator to provide a magnified image that can be displayed.

BRIEF DESCRIPTION OF THE DRAWINGS

FIGS. 6a, 6b and 6c are printed circuit board (PCB) diagrams for the LEDs, the LED driver and the power supply for the embodiment of FIG. 1.

DETAILED DESCRIPTION

Figure 1:
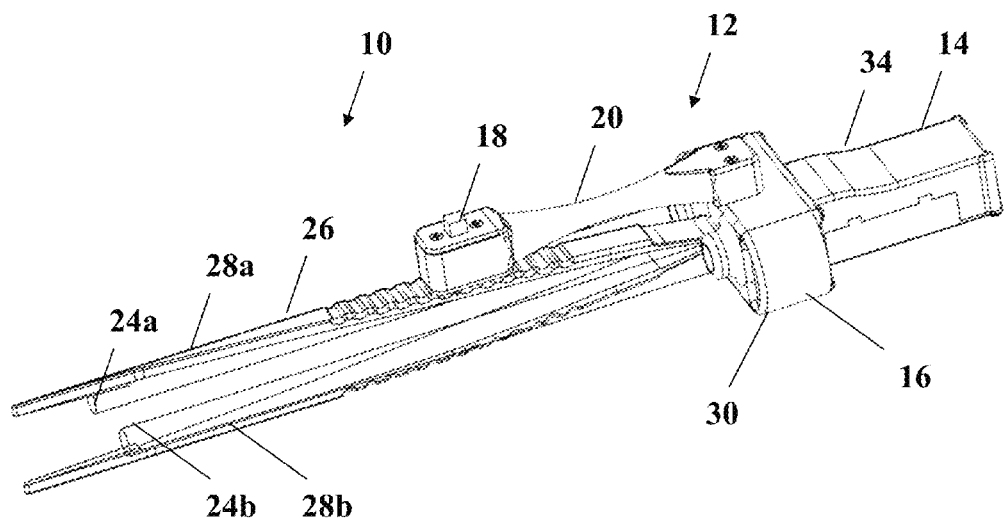
FIG. 1 is a perspective view of an embodiment of the present invention.

The invention resides in an apparatus and method of use for enhancing the ability to locate and remove foreign objects from physiological/anatomical surroundings such as a wound (such as debris or blast shrapnel) or from a surgery (such as an article mistakenly left in) by enhancing the visual contrast of the objects that must be removed from the other things being observed such as anatomical parts that produce complicated visual background.

Exemplary applications of the invention are: (1) in surgical wound debridement; (ii) in open surgical procedures for designating and removal of missed or lost medical supply; (iii) in forensic sciences for investigating evidence or in interpreting complicated mixtures; (iv) in life sciences research and laboratory tests for designating and separating objects in slurries and solutions.

The invention can be implemented in a number of ways.

The invention in one embodiment is a multicolor light source apparatus to which a forceps can be attached. The light source is combined with a waveguide or lightguide that projects the light to a favored position with respect to operation of the forceps such that the light illuminates an area that is being worked on. In one embodiment, the light color is selectable from a multicolored light source so that by the selection a useful contrast can be made of the foreign material relative to normal material. In one embodiment, the illumination device is an LED chip with a plurality of differently colored dies. A selection control allows selection of a desired one of the dies. A trigger switch can be used to sequentially turn on the dies in order to find the color that provides the most useful contrast. In another embodiment, the dies can be mixed and the mixture can be varied to provide incremental or graduated spectral variation in order to find the best color mix for good contrast. Also, certain light mixtures can be stored in a preprogrammed set for specific objects for which preferred contrasting illumination is known.

An exemplary light source is the multicolor LED chip. The chip may include dies of blue, green, red, white and UV LEDs (the UV LED is useful for the designation of highly luminescent objects). Optional simplified LED chip configurations are: (i) RGB without UV, and white light may be produced by mixing these colors in certain proportions using the CIE chart; (ii) RBGW without UV where white is produced by the white die. Specific image enhancing additive colors can be preset in the memory of a preprogrammed chip for known objects common to a specific usage, such as foreign objects in combat wounds.

In various embodiments, the light source and its controls are provided in a head portion which also has an element allowing attachment of a forceps whereby the illumination is directed relative to clamping elements of the forceps such that the area being worked on is most directly illuminated.

Also, in various embodiments, the light from the light source in the head portion is directed to the desired area of illumination by waveguides such one or more optical fibers or by one or more rigid light pipes. The light will delivered to a point at or near the tips of the forceps, such a 1 to 1½ inches beyond the tips. One goal is to provide shadowless illumination of the examined area in between the tips of the forceps. In one embodiment the light is projected so as to be centralized between the arms of the forceps The type of forceps commonly called tweezers forceps (historically called dissecting forceps) has an opposed pair of arms or clamps with a spring joint biasing the arms open, at the proximal end and clamping tips at the distal end, usable by pressing the arms together against the spring force.

In the present invention, the illumination head has a docking element into which the proximal end of the forceps is placed.

Now, various embodiments of the invention will be described with reference to the figures.

Figure 2:
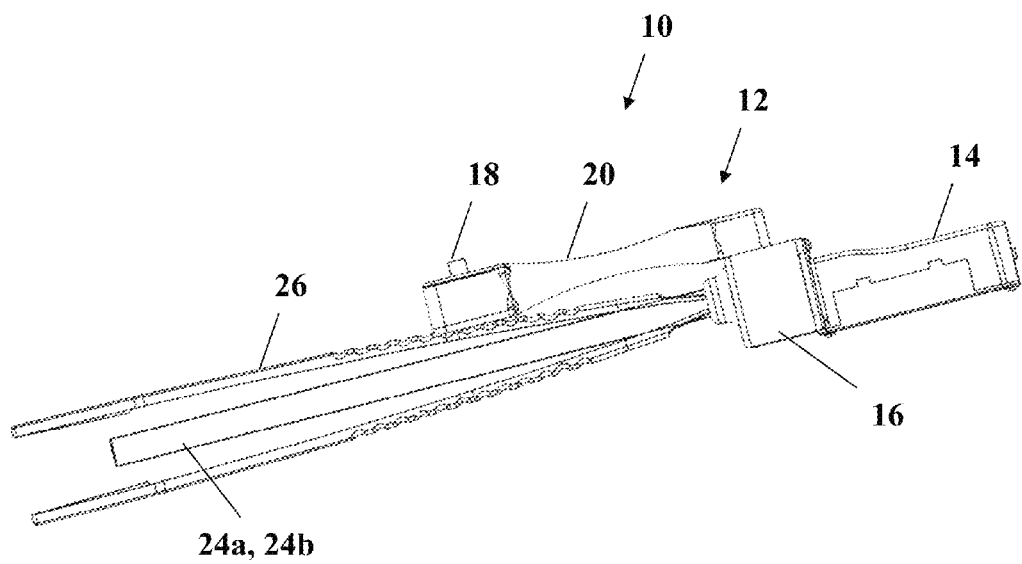
FIG. 2 is a side view of the embodiment of FIG. 1.
Figure 3:
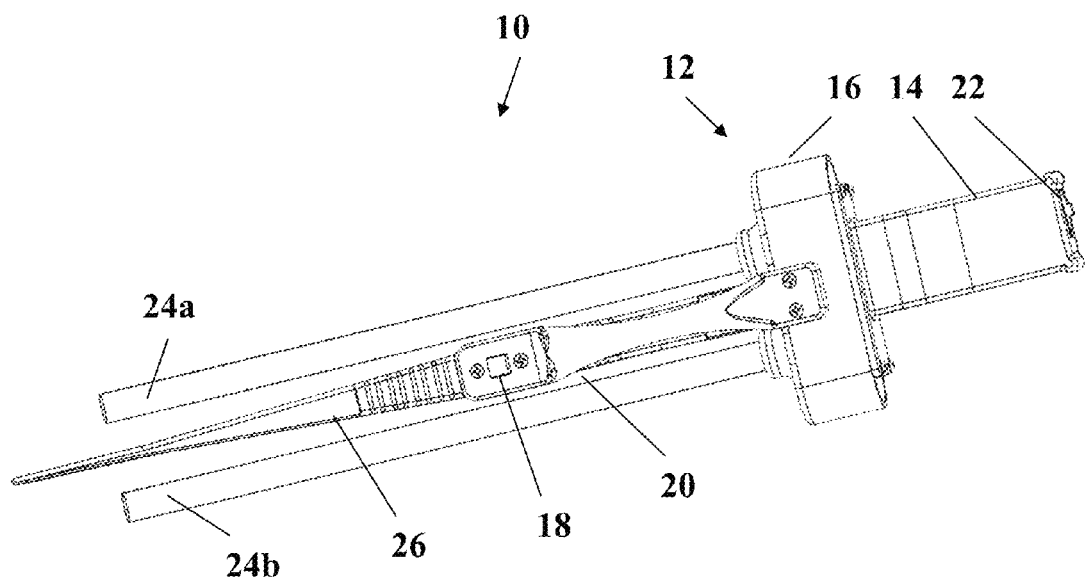
FIG. 3 is a top view of the embodiment of FIG. 1.

FIGS. 1, 2 and 3 show an illuminator 10 in accordance with the principles of this invention. The illuminator comprises a head 12 comprising a battery compartment 14 and an electronics compartment 16 and an extension leg 20. A control switch for color selection is shown at 18 mounted on the extension leg 20 that places the switch 18 conveniently for a user of the forceps. An on-off switch 22 is located at the rear of the battery compartment 14. Waveguides in the form of light pipes 24a and 24b extend from the electronics compartment 16 and can be seen to be spaced apart from one another in a plane orthogonal to the arms 28a and 28b of an illustrative forceps 26 which has been docked to the illuminator 10, as will be described below. The light pipes 24a and 24b are secured to the cover 30 of the electronics compartment 16 in apertures 32a and 32b such as by set screws (not shown) or press fitting or other securing mean.

Figure 4:
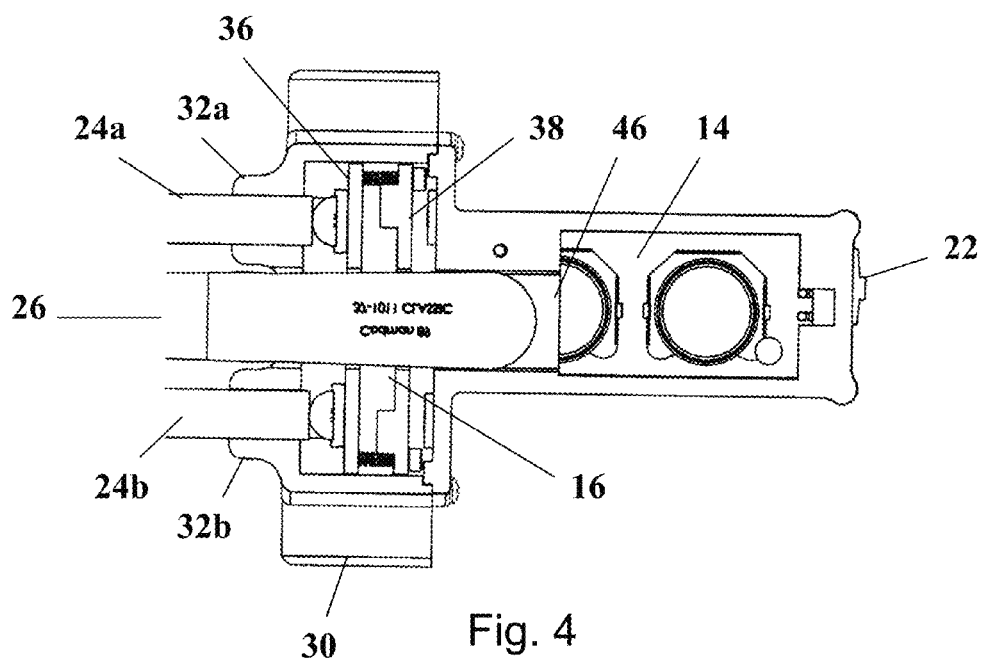
FIG. 4 is a view showing the interior of the embodiment of FIG. 1.
Figure 5:
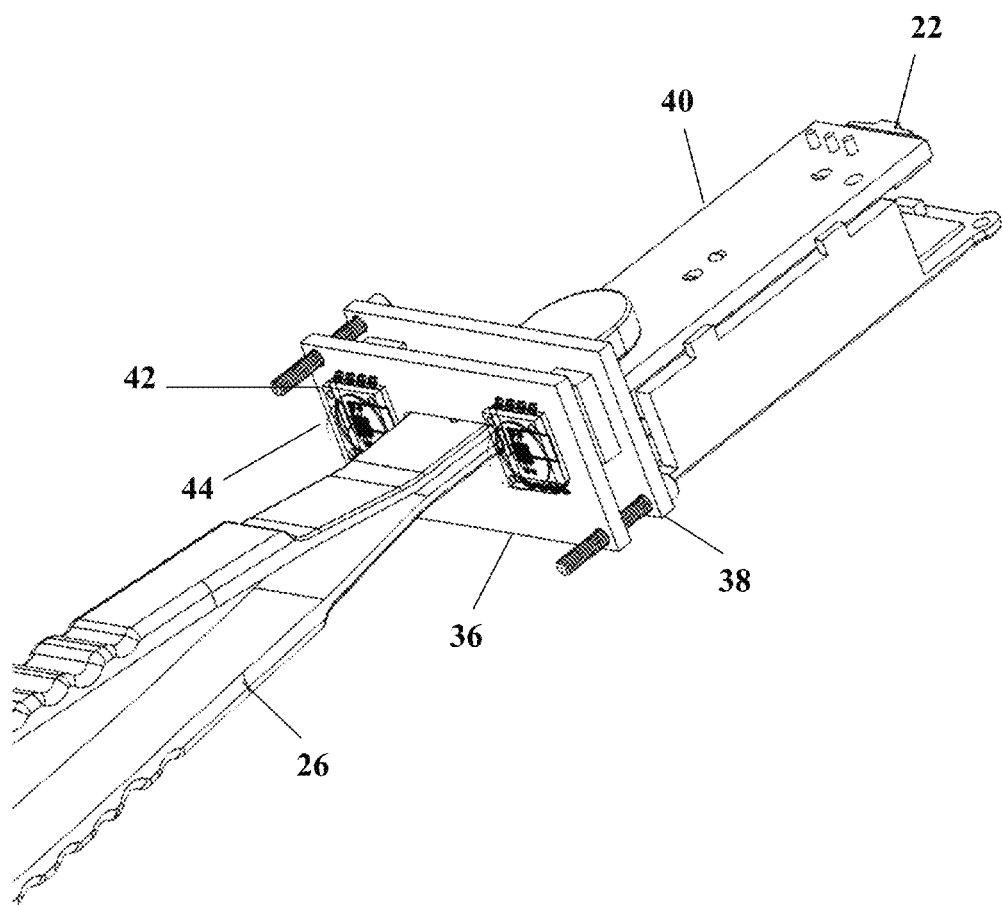
FIG. 5 is a perspective view with the covers removed of the embodiment of FIG. 1.
Figure 9:
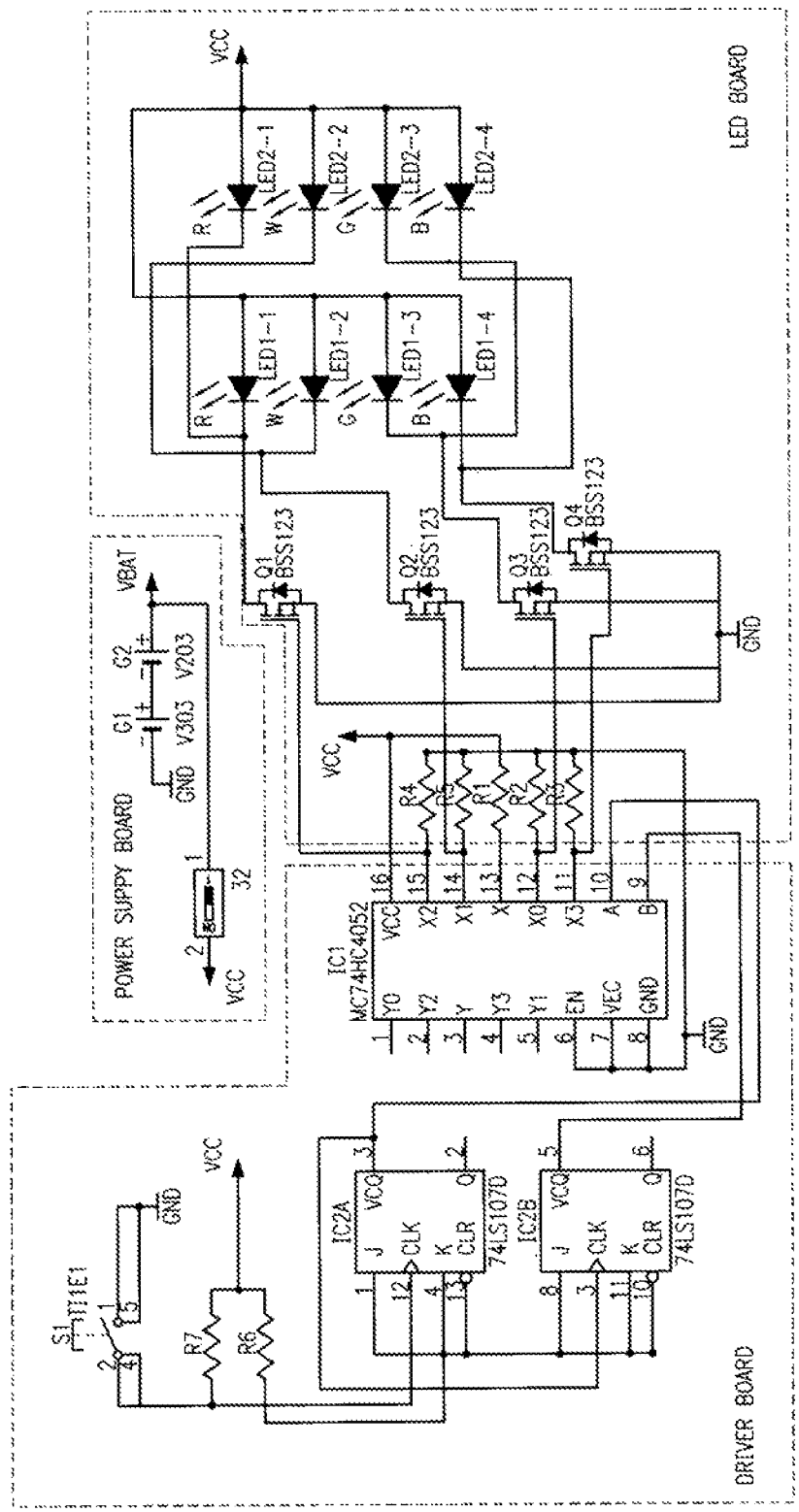
FIG. 9 is a circuit diagram of an embodiment of the invention.

FIG. 4 is a view of the illuminator with the interiors of the electronics compartment 16 and the battery compartment 14 shown. Also, FIG. 5 shows a view of the interior of the electronics compartment 16 and of the battery compartment 14 with their covers removed. In these views and with further reference to FIGS. 6a, 6b and 6c there is shown the electronics of the apparatus in which there is an LED PC board 36 (FIG. 6a), a driver PC board 38 (FIG. 6b) and a power supply PC board 40 (FIG. 6c). Both sides of each of the three PC boards are shown in FIGS. 6a, 6b and 6c. The exemplary circuit diagram is shown in FIG. 9 and is outlined to show the circuitry for each of the three PC boards. On the front of the LED PC board 36, a pair of LED chips 42 are mounted, each one having a lens 44.

Figure 7:
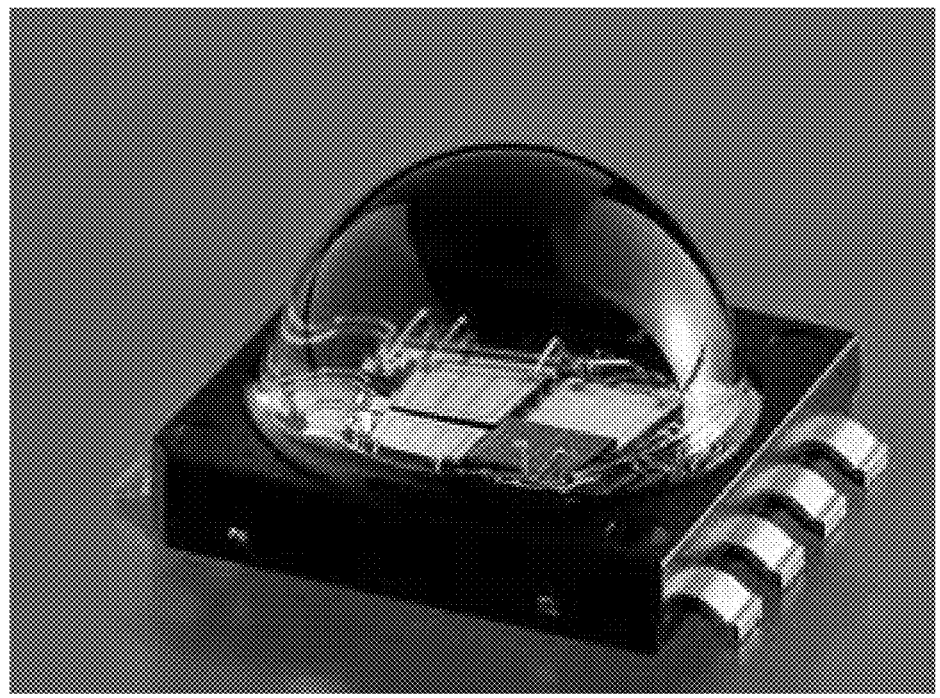
FIG. 7 is a view of an LED chip having red, blue, green and white dies.

The LED chip 42 is also shown in FIG. 7. Exemplary of these chips is the Cree X Lamp MC-E LED (RGBW) of Cree. Inc. of Durham, N.C. which has red, green, blue and white LED dies.

The apertures 32a and 32b are in registry with lenses 44 and thus with the LED chips 40 so that the light pipes 24a and 24b are in the right place for receiving and transmitting light from the LED chips.

Figure 8:
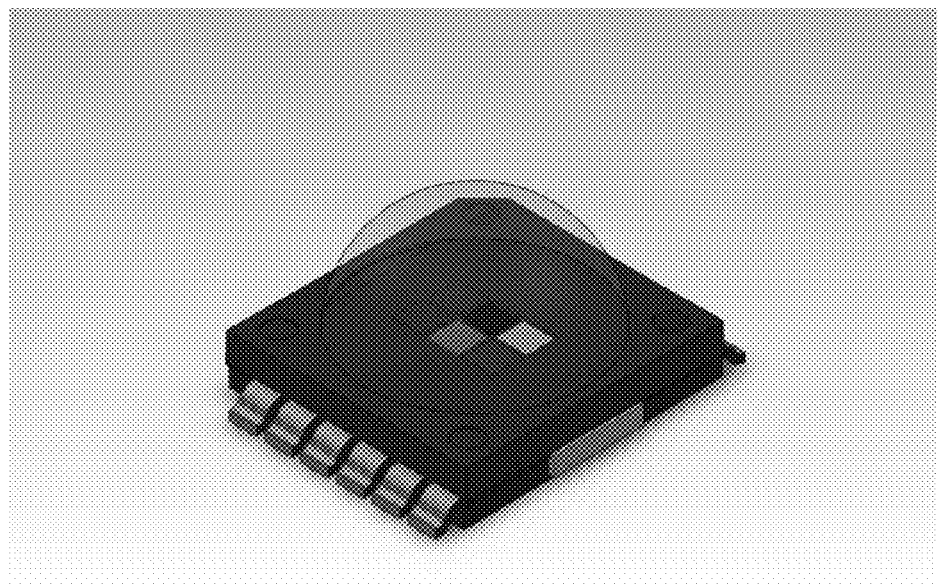
FIG. 8 is an illustration of an LED chip with RGBW and violet dies.

Also, in FIG. 8 there is shown an exemplary LED chip that has dies of RGBW and UV.

The forceps 26 is shown in FIG. 4 inserted and held on the illumination head 10. It passes loosely through openings in the cover 30 and the LED boards 36 and 38 having its proximal end slid into place in a slot or docking portal 46 in the battery compartment 14 by a fit made tight enough to hold it in place during use but to allow it to be pulled out by hand. While the forceps proximal end passes through the cover 30 and the PC boards 36 and 38, that is a loose fit. Generally, other ways of holding the forceps in place can be configured such as a positive detent in which a bump or hole is in the forceps and an opposite element in the illuminator.

The illuminator 10 is adapted to receive forceps with arms of varying length and light pipes 24a and 24b may be replaced by light pipes of differing lengths to adjust to the lengths of the forceps arms. The light pipes are chosen to be of lengths to deliver light ahead of the distal ends of the forceps in order to illuminate the area being worked on to provide illumination and by reason of selected colors, contrast to identify foreign bodies. As shown the light pipes end short of the ends of the forceps arms so as to not interfere with use of the forceps.

In FIG. 9 the electronics of the apparatus is shown. The Driver Board portion contains the switch 18 connected to the flip-flop triggers so that sequential pressing of the switch 18 will be processed through the multiplexer/demultiplexer chip to command sequential selection of the dies of the LED chips, a pair of four die chips (the LED chips 42) being illustrated in the circuit in the LED Board portion of the circuit diagram. The Power Supply portion shows the battery and the on-off switch 22.

In use, the forceps is fitted into the docking portal where it is held sufficiently tightly to use the device but allowing it to be removed. The user can start with any selected color of the RBGW chips by pressing the switch 18 which sequentially cycles illumination of the RGBW dies. It is anticipated that with experience for a particular use, the user will start with a color known to give good contrast for the anticipated foreign material. This will be especially the case for combat wounds where the contrasting color for foreign bodies from combat wounds will be known by the user. In some cases, the user may start with white light in order to assess the general condition, and then cycle to the best color for contrast.

The embodiment described above has a selection functioning mode of sequential selection of specific colors from a multicolor source, in this embodiment that source being the LED chip and the selections in one embodiment being in sequence, red, green, blue and white. Other selection functioning modes are available such as graduated or universally adjustable selection from a color range such as from red to blue, or from red to the ultra violet or preprogrammed color mixes which are described in the embodiments following. Using one or more of the selection functioning modes allows the apparatus and method to be used for enhancing light in surgical debridement most conveniently for selecting the best contrast. In the case of the sequential selection mode, each of a sequence of colors is available from an LED chip in which each die of the chip is one of the sequential selections. But also, special mixtures of light from the dies can be programmed into the electronics, for example a particular light mixture might be optimal for enhancing contrast of foreign material found in combat wounds.

Figures 10A, 10B:
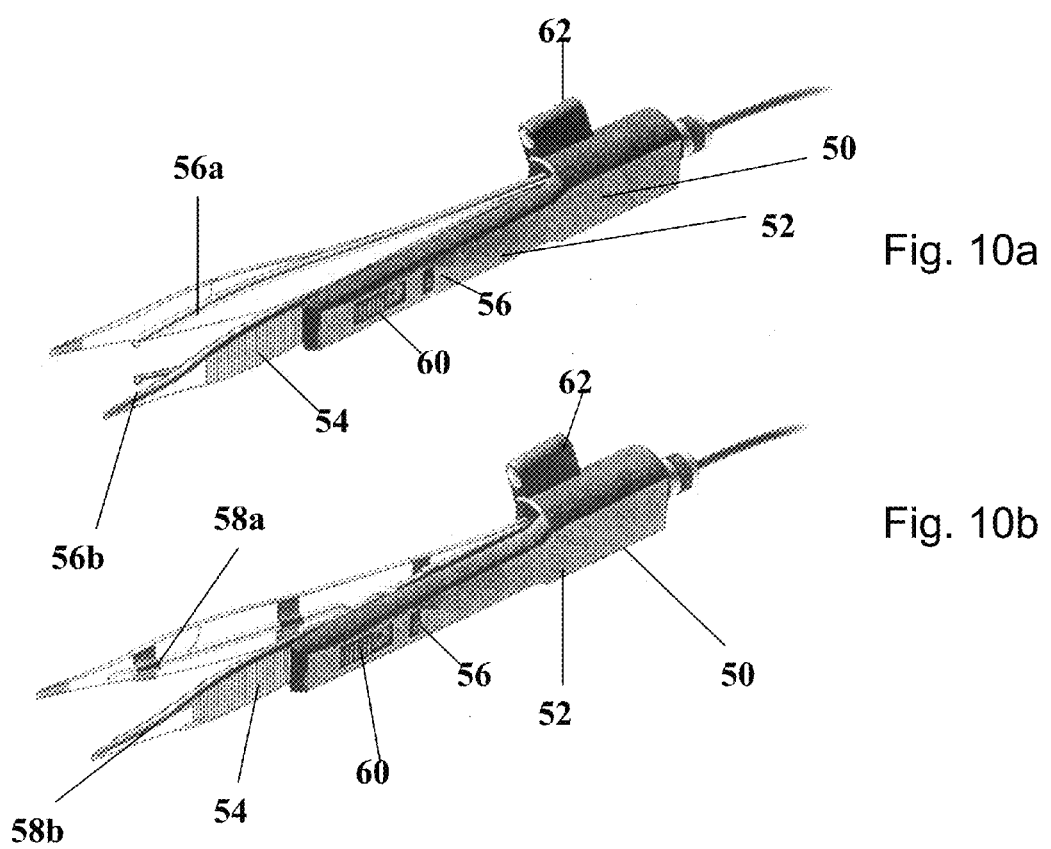
FIGS. 10a and 10b are alternative embodiments of the invention.
Figure 11:
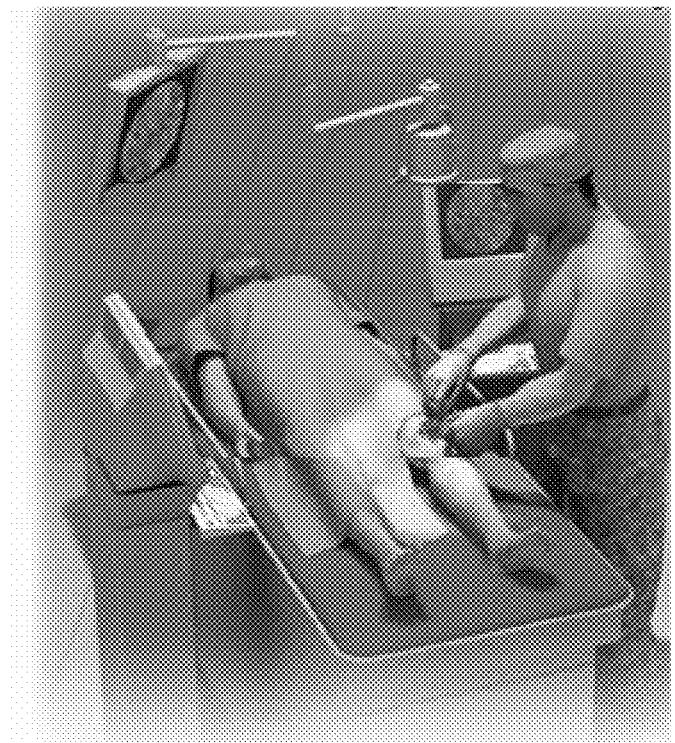
FIG. 11 is an illustration of the invention in use along with remoter displays

Other embodiments of the invention are shown in FIGS. 10A and 10B. In these embodiments the illuminator 50 has an extended arm 52 aligned with one side of a forceps 54. This allows easy access to varying the light by operating switches in the extended arm 52. The embodiment of FIG. 10A has self supported light transmitting waveguides that are slightly curved light pipes 56a and 56b. The embodiment of FIG. 10B has light transmitting means that are secured to each arm of the forceps, and it is anticipated that optical fibers 58a and 58b (not shown) will be used. The light sourcing and selection can be as described above. But, each of these embodiments show a version of the invention in which color mixing from a single LED chip of multiple dies is enabled by varying the current to each die so as to vary the intensity of light from each die to provide a color mix, in that way allowing a universal adjustment of color. The extended arm 52 has a three position switch 60 having an off position and two active positions, one for color mixed light and one for white light. When in the position for color mixed light, the wheel 56 which is wired into the circuitry for the LED chip, can be rotated to cause color mixing. Also, there is shown a micro video camera 62 which can transmit the scene at the wound to a display. FIG. 11 illustrates an exemplary view of a doctor and patient with displays available to the doctor.

The method of the invention using the embodiments described above is to insert the forceps into the illuminator. The mounting and dismounting of the forceps contemplates that the forceps will be sterilized for reuse.

Then the user turns on the illuminator and commences to position it to illuminate the area under treatment. To begin, a white light might be used to get a general appraisal of the situation. Then a contrast illumination will be selected. In the case of sequential illumination, the activating button or other means is used to cycle through the selections which can be simply the illumination of each die in turn. Then the forceps are used to pick out the foreign bodies/objects. Alternatively the electronics can be configured to allow universal adjustment through the spectral range given by the dies. Also, it is possible to provide selected color mixes based on experience for expected foreign bodies.

What has been described herein is considered merely illustrative of the principles of this invention. Accordingly, it is well within the purview of one skilled in the art to provide other and different embodiments within the spirit and scope of the invention as encompassed by the following claims.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable.

The invention claimed is:

1. A method for surgical debridement by applying color illumination to enhance the contrast of foreign material to anatomical material in an area under surgical debridement comprising:
   providing an illuminator portion having a docking element for docking a forceps into which a forceps can be removable attached at a proximal end thereof and held in place by frictional engagement or by positive detent engagement with the docking element to orient a forceps such that clamping portions of the forceps will define a plane and the illuminator portion and having an LED chip on each of opposite sides of the docking element having at least red, green and blue dies defining an LED chip pair defining a plane that is orthogonal to the plane defined by the clamping portions;
   providing a user responsive controller having a selection functioning mode of the LED chip pair wherein the selection functioning mode provides at least a mode of sequentially graduated or universally sequentially adjustable selecting from a color range of the same color from the two LED chips and having an activation function for selecting a color within the range upon the establishment of enhanced contrasting illumination of foreign material;
   providing a pair of self-supporting light pipes attached to the illuminator portion each one positioned to receive light from one of the LED chips and extending a distance to terminate behind the clamping portions of the forceps and in the plane defined by the LED chips for transmitting light from the LED chips to illuminate the selected color an area proximately in front of and between the clamping portions of the forceps;
   providing a forceps attached to the illuminator portion at the docking element and wherein illumination from the pair of light pipes will illuminate an area proximately in front of and between the clamping portions;
   positioning at or moving the forceps in an anatomical area under surgical debridement;
   operating the selection functioning mode and the activation function to select a color that provides enhanced contrast of foreign material relative to anatomical material in the area;
   removing foreign material.

2. A method for surgical debridement by applying color illumination to enhance the contrast of foreign material to anatomical material in an area under surgical debridement comprising:
   providing an illuminator portion having a docking element for docking a forceps into which the forceps can be removably attached at a proximal end thereof, whereby the clamping portions of the forceps will define a plane;
   providing two or more illumination elements affixed to the docking element, defining a plane that is orthogonal to the plane defined by the clamping portions;
   providing a forceps attached to the illuminator portion at the docking element and wherein an area proximately in front of and between the clamping portions is illuminated;
   providing a user responsive controller having a selection functioning mode of the illuminator portion wherein the selection functioning mode provides at least a mode of sequentially graduated or universally sequentially adjustable selecting from a color range of the same color from the illuminator portion and having an activation function for selecting a color within the range upon the establishment of enhanced contrasting illumination of foreign material;

providing a pair of self-supporting light guides attached to the illuminator portion each one positioned to receive light from one of the illumination elements and extending a distance to terminate behind the clamping portions of the forceps and in the plane defined by the illumination elements for transmitting light to illuminate the selected color an area proximately in front of and between the clamping portions of the forceps;

operating the selection functioning mode and the activation function to select a color that provides enhanced contrast of foreign material relative to anatomical material in the area positioning at or moving the forceps in an anatomical area under surgical debridement;

removing foreign material.

3. A method for surgical debridement as in claim 2 wherein the illuminator emits light from one or more light-emitting diodes.

4. A method for surgical debridement as in claim 2 wherein the illuminator emits light from a combination of light-emitting diodes comprising one or more of red, green, blue, and white light.

5. A method for surgical debridement as in claim 2 wherein the illuminator emits light in the ultra-violet range.

\* \* \* \* \*